(12) United States Patent
Graindorge et al.

(10) Patent No.: US 7,476,668 B2
(45) Date of Patent: Jan. 13, 2009

(54) THIADIAZINE DERIVATIVES AND USE THEREOF AS POSITIVE AMPA RECEPTOR MODULATORS

(75) Inventors: Emmanuel Graindorge, Liege (BE); Pierre Francotte, Liege (BE); Stéphane Boverie, Anthisnes (BE); Pascal De Tullio, Jupille (BE); Bernard Pirotte, Oupeye (BE); Pierre Lestage, La Celle Saint Cloud (FR); Laurence Danober, Montesson (FR); Pierre Renard, Le Chesnay (FR); Daniel-Henri Caignard, Le Pecq (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 375 days.

(21) Appl. No.: 10/555,743

(22) PCT Filed: May 4, 2004

(86) PCT No.: PCT/FR2004/001070

§ 371 (c)(1),
(2), (4) Date: Nov. 4, 2005

(87) PCT Pub. No.: WO2004/099217

PCT Pub. Date: Nov. 18, 2004

(65) Prior Publication Data

US 2007/0004709 A1    Jan. 4, 2007

(30) Foreign Application Priority Data

May 5, 2003   (FR) .................................. 03 05448

(51) Int. Cl.
*C07D 513/04*   (2006.01)
*A61K 31/542*   (2006.01)

(52) U.S. Cl. ..................................... 514/222.8; 544/10
(58) Field of Classification Search .................. 544/10; 514/222.8
See application file for complete search history.

(56) References Cited

U.S. PATENT DOCUMENTS 3,733,409 A * 5/1973 Topliss .................... 514/222.8

FOREIGN PATENT DOCUMENTS

FR    2801587    6/2001

| WO | WO9812185 | 3/1998 |
|----|-----------|--------|
| WO | WO9903861 | 1/1999 |
| WO | WO9942456 | 8/1999 |

OTHER PUBLICATIONS

Huang et al. J. Org. Chem., vol. 44, No. 23, 4046-4050 (1979).*
Alt et al. Current Pharmaceutical Design, 2005, 11, 1511-1527.*
Black et al Psychopharmacology (2005) 179: 154-163.*
Daniel DeNoon, Schizophrenia Drug Face-Off: No Clear Winner http://www.webmd.com/content/Article/112/110297.htm?printing=true down loaded on May 22, 2006.*
International Search Report: PCT FR2004 001070—Sep. 6, 2004.

* cited by examiner

*Primary Examiner*—Kahsay T. Habte
(74) *Attorney, Agent, or Firm*—Hueschen and Sage

(57) ABSTRACT

Compounds of formula (I):

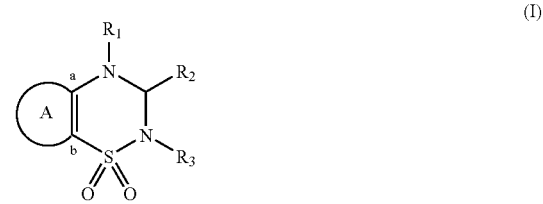

wherein:
A represents thienyl, furyl, pyrrolyl, oxathiol, thiazole, isothiazole, oxazole or imidazole,
----- represents a single bond or a double bond,
$R_1$ represents hydrogen, linear or branched $(C_1-C_6)$alkyl optionally substituted by one or more groups selected from halogen or $(C_1-C_6)$alkoxy-$(C_1-C_6)$alkyl,
$R_2$ represents hydrogen or linear or branched $(C_1-C_6)$alkyl group optionally substituted by one or more halogen,
$R_3$ represents hydrogen or a group selected from linear or branched $(C_1-C_6)$alkyl, CONHR' and $SO_2$NHR' wherein R' represents linear or branched $(C_1-C_6)$alkyl,
its enantiomers and diastereoisomers, and addition salts thereof with a pharmaceutically acceptable acid or base.

Medicinal products containing the same, which are useful as AMPA inhibitors.

11 Claims, No Drawings

THIADIAZINE DERIVATIVES AND USE THEREOF AS POSITIVE AMPA RECEPTOR MODULATORS

The present invention relates to new thiadiazine compounds, to a process for their preparation and to pharmaceutical compositions containing them.

It has now been recognised that the excitatory amino acids, especially glutamate, play a crucial role in the physiological processes of neuronal plasticity and in the mechanisms underlying learning and memory. Pathophysiological studies have clearly shown that a defect of glutamatergic neurotransmission is closely associated with the development of Alzheimer's disease (Neuroscience and Biobehavioral Reviews, 1992, 16, 13-24; Progress in Neurobiology, 1992, 39, 517-545).

In addition, some works have in recent years demonstrated the existence of sub-types of excitatory amino acid receptors and their functional interactions (Molecular Neuropharmacology, 1992, 2, 15-31).

Among those receptors, the AMPA (α-amino-3-hydroxy-5-methyl-4-isoxazole-propionic acid) receptor appears to be involved to the greatest extent in the phenomena of physiological neuronal excitability and, especially, in those phenomena involved in memorisation processes. For example, it has been shown that learning is associated with an increase in the binding of AMPA to its receptor in the hippocampus, one of the areas of the brain essential to processes of memory and cognition. Likewise, nootropic agents such as aniracetam have very recently been described as modulating the AMPA receptors of neuronal cells in a positive manner (Journal of Neurochemistry, 1992, 58, 1199-1204).

In the literature, compounds having a benzamide structure have been described as possessing this same mechanism of action and improving memory performance (Synapse, 1993, 15, 326-329). Compound BA 74 in particular is the most active of those new pharmacological agents.

Finally, patent specification EP 692 484 describes a benzothiadiazine compound having a facilitating action on the AMPA current, and patent application WO 99/42456 describes inter alia particular benzothiadiazine compounds as modulators of AMPA receptors.

The thiadiazine compounds to which the present invention relates, besides being new, surprisingly exhibit pharmacological activity on the AMPA current that is markedly superior to the activity of the compounds having similar structures described in the prior art. They are useful as AMPA modulators for the treatment or prevention of disorders of memory and cognition that are associated with age, with syndromes of anxiety or depression, with progressive neurodegenerative diseases, with Alzheimer's disease, with Pick's disease, with Huntington's chorea, with schizophrenia, with the after-effects of acute neurodegenerative diseases, with the after-effects of ischaemia and with the after-effects of epilepsy.

More specifically, the present invention relates to compounds of formula (I):

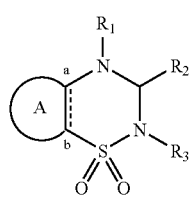

(I)

wherein:

A, with the two carbon atoms carrying it, forms a thienyl, furyl or pyrrolyl group selected from the groups $A_1$, $A_2$, $A_3$:

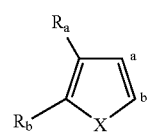

$A_1$

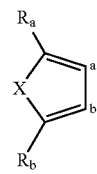

$A_2$

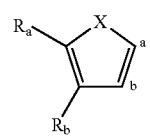

$A_3$ wherein X in each case represents a sulphur, oxygen or nitrogen atom and $R_a$ and $R_b$, which may be identical or different, each independently of the other represents a hydrogen atom, a linear or branched ($C_1$-$C_6$)alkyl group (optionally substituted by one or more fluorine atoms), a linear or branched ($C_1$-$C_6$)alkoxy group, a halogen atom, a hydroxy group, an amino group optionally substituted by a linear or branched ($C_1$-$C_6$)-alkylcarbonyl group, by one or two linear or branched ($C_1$-$C_6$)alkyl groups, a carboxyl group or a linear or branched ($C_1$-$C_6$ an oxathiol group selected from the groups $A_4$, $A_5$, $A_6$, $A_7$:

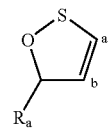

$A_4$

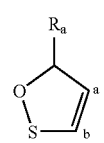

$A_5$

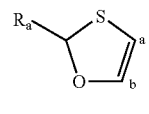

$A_6$

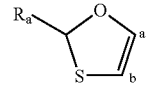

$A_7$ wherein $R_a$ is as defined hereinbefore, a thiazole group selected from the groups $A_8$, $A_9$:

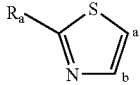

$A_8$

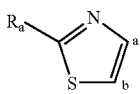

$A_9$ wherein $R_a$ is as defined hereinbefore,
an isothiazole group selected from the groups $A_{10}$, $A_{11}$:

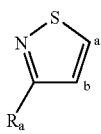

$A_{10}$

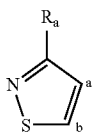

$A_{11}$ wherein $R_a$ is as defined hereinbefore,
an oxazole group selected from the groups $A_{12}$, $A_{13}$, $A_{14}$, $A_{15}$:

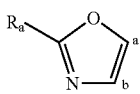

$A_{12}$

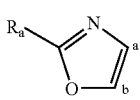

$A_{13}$

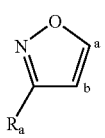

$A_{14}$

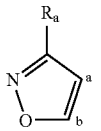

$A_{15}$ wherein $R_a$ is as defined hereinbefore, or an imidazole group of formula $A_{16}$:

$A_{16}$ wherein $R_a$ is as defined hereinbefore,
- - - - - represents a single bond or a double bond,
$R_1$ represents a hydrogen atom, a linear or branched ($C_1$-$C_6$)alkyl group optionally substituted by one or more fluorine atoms, or a plurality of halogen atoms other than fluorine, or a ($C_1$-$C_6$)alkoxy-($C_1$-$C_6$)alkyl group in which each alkyl moiety may be linear or branched,
$R_2$ represents a hydrogen atom or a linear or branched ($C_1$-$C_6$)alkyl group optionally substituted by one or more fluorine atoms, or a plurality of halogen atoms other than fluorine,
$R_3$ represents a hydrogen atom or a group selected from linear or branched ($C_1$-$C_6$)alkyl, CONHR' and $SO_2$NHR' wherein R' represents a linear or branched ($C_1$-$C_6$)alkyl group, to their enantiomers and diastereoisomers, and also to addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc. . . .

Among the pharmaceutically acceptable bases there may be mentioned, without implying any limitation, sodium hydroxide, potassium hydroxide, triethylamine, tert-butylamine, etc.

The group A to which preference is given is a thienyl group selected from the groups $A_1$, $A_2$ and $A_3$ wherein X represents a sulphur atom.

Even more preferably, the group A to which preference is given is a thienyl group selected from the groups $A_1$ and $A_2$ wherein X represents a sulphur atom.

The groups $R_a$ and $R_b$ to which preference is given, independently of one another, are a hydrogen atom and a chlorine atom.

The group $R_1$ to which preference is given is a hydrogen atom or a linear or branched ($C_1$-$C_6$)alkyl group, preferably a methyl, ethyl or isopropyl group.

The group $R_2$ to which preference is given is a hydrogen atom.

The group $R_3$ to which preference is given is a hydrogen atom or a CONHR' group wherein R' is as defined for formula (I).

The compounds to which preference is given according to the invention are:
  6-chloro-4-ethyl-3,4-dihydro-2H-thieno[3,2-e][1,2,4]thiadiazine 1,1-dioxide,
  6-chloro-4-isopropyl-3,4-dihydro-2H-thieno[3,2-e][1,2,4]thiadiazine 1,1-dioxide,
  5,7-dichloro-4-methyl-3,4-dihydro-2H-thieno[3,4-e][1,2,4]thiadiazine 1,1-dioxide.

The invention relates also to a process for the preparation of compounds of formula (I), characterised in that there is used as starting material a compound of formula (II):

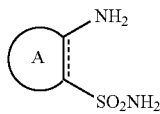
(II)

wherein A and ⁻⁻⁻⁻ are as defined for formula (I),
which compound of formula (II) is cyclised in the presence of a compound of formula (III):

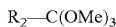
(III)

wherein $R_2$ is as defined for formula (I), to yield a compound of formula (IV):

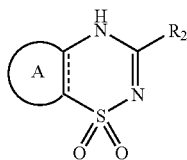
(IV)

wherein A, $R_2$ and ⁻⁻⁻⁻ are as defined hereinbefore,
which compound of formula (IV) is:
either reacted with a reducing agent to yield a compound of formula (I/a), which is a particular case of the compounds of formula (I):

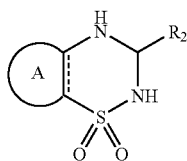
(I/a)

wherein A, $R_2$ and ⁻⁻⁻⁻ are as defined hereinbefore,
which compound of formula (I/a) is optionally reacted with di(tert-butyl) dicarbonate to yield a compound of formula (V):

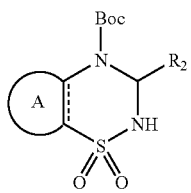
(V)

wherein Boc represents the group tert-butoxycarbonyl and A, $R_2$ and ⁻⁻⁻⁻ are as defined hereinbefore,
which compound of formula (V) is reacted with a compound of formula (VI):

(VI)

wherein $R'_3$ represents a linear or branched $(C_1-C_6)$alkyl group or a CONHR' or $SO_2$NHR' group, wherein R' is as defined for formula (I), and $Y_3$ represents a leaving group, to yield, after deprotection, a compound of formula (I/b), which is a particular case of the compounds of formula (I):

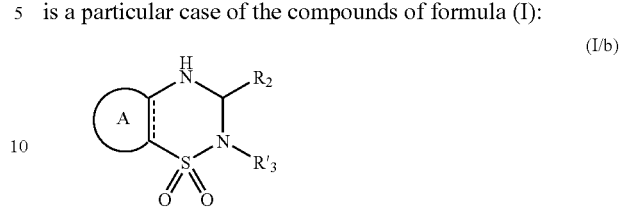
(I/b)

wherein A, $R_2$, $R'_3$ and ⁻⁻⁻⁻ are as defined hereinbefore,
or reacted, in a basic medium, with a compound of formula (VII):

(VII)

wherein $R'_1$ represents a linear or branched $(C_1-C_6)$alkyl group optionally substituted by one or more fluorine atoms or a plurality of halogen atoms, and $Y_1$ represents a leaving group, to yield a compound of formula (VII):

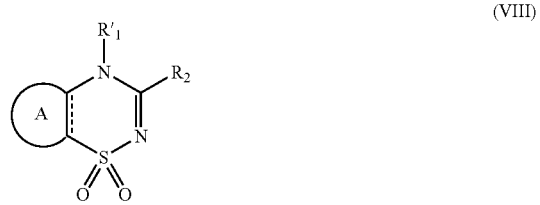
(VIII)

wherein A, $R'_1$, $R_2$ and ⁻⁻⁻⁻ are as defined hereinbefore,
which compound of formula (VIII) is reacted with a reducing agent to yield a compound of formula (I/c), which is a particular case of the compounds of formula (I):

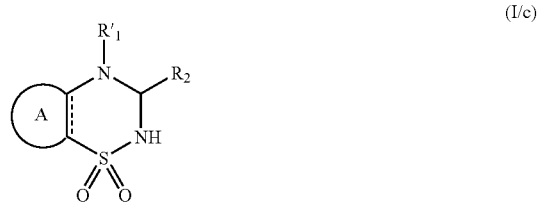
(I/c)

wherein A, $R'_1$, $R_2$ and ⁻⁻⁻⁻ are as defined hereinbefore,
which compound of formula (I/c) is optionally reacted with a compound of formula (VI) as defined hereinbefore to yield a compound of formula (I/d), which is a particular case of the compounds of formula (I):

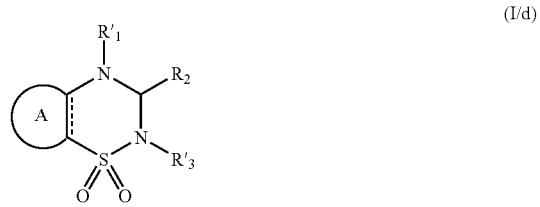
(I/d)

wherein A, $R'_1$, $R_2$, $R'_3$ and ⁻⁻⁻⁻ are as defined hereinbefore,
which compounds of formulae (I/a) to (I/d) constitute the totality of the compounds of formula (I), which are purified, where necessary, according to a conventional purification technique, which are separated, if desired, into their enantiomers or diastereoisomers according to a conventional separation technique, and which are converted, if desired, into their addition salts with a pharmaceutically acceptable acid or base.

The compounds of the present invention, besides being new, have AMPA-receptor-activating properties which make them useful in the treatment of cognitive defects associated with cerebral ageing and with neurodegenerative pathologies such as Alzheimer's disease, Parkinson's disease, Pick's disease, Korsakoff's disease, frontal and sub-cortical dementias, as well as in the treatment of schizophrenia.

The invention relates also to pharmaceutical compositions comprising as active ingredient at least one compound of formula (I) together with one or more appropriate inert, non-toxic excipients. Among the pharmaceutical compositions according to the invention there may be mentioned more especially those that are suitable for oral, parenteral (intravenous or subcutaneous) or nasal administration, tablets, dragees, sublingual tablets, gelatin capsules, lozenges, suppositories, creams, ointments, dermal gels, injectable preparations, drinkable suspensions, etc.

The useful dose can be adapted according to the nature and severity of the disorder, the administration route and the age and weight of the patient. The dose varies from 1 to 500 mg per day, in one or more administrations.

The Examples that follow illustrate the invention, without limiting it in any way.

The starting materials used are products which are known or are prepared according to known procedures.

The structures of the compounds described in the Examples were determined according to customary spectrophotometric techniques (infra-red, NMR, mass spectrometry).

Preparation 1:
6-Chloro-4H-thieno[3,2-e][1,2,4]thiadiazine 1,1-dioxide 250 mg of 3-amino-5-chloro-2-thiophenesulphonamide hydrochloride (*J. Med Chem.*, 2002, 4171-4187) are placed in 2.5 ml of triethyl o-formate. The solution is heated at about 60° C. for 30 minutes. A granular yellow precipitate forms and is collected by filtration, washed with diethyl ether and then dried.

Melting point: 260-262° C. IR (KBr): 3214, 3103, 3061, 2926, 1602, 1569, 1515, 1446, 1378, 1366, 1287, 1220, 1177, 1147, 978, 840, 824, 750, 628, 543 cm$^{-1}$ Preparation 2:
5,7-Dichloro-4H-thieno[3,4-e][1,2,4]thiadiazine 1,1-dioxide Step A: 2,5-Dichloro-4-nitro-3-thiophenesulphonyl chloride A mixture of 30 ml of sulphuric acid and 30 ml of fuming nitric acid is cooled by means of a salted ice bath. 10 g of 2,5-dichloro-3-thiophenesulphonyl chloride are slowly added to the mixture. The solution is stirred at ambient temperature for 3 hours. The solution is then poured onto ice. The yellowish precipitate that forms is collected by filtration, washed with water and dried.

IR (KBr): 3525, 3410, 2917, 1673, 1552, 1442, 1388, 1176, 1085 cm$^{-1}$

Step B:
2,5-Dichloro-4-nitro-3-thiophenesulphonamide 11 g of the compound of Step A above are dissolved in 150 ml of dioxane. This solution is added dropwise to 300 ml of a 10% ammonium hydroxide solution. After one hour, the ammonia and the dioxane are evaporated off under reduced pressure. The white precipitate that forms is collected by filtration, washed with water and dried.

Melting point: 125-126° C. IR (KBr): 3390, 3291, 1541, 1505, 1440, 1369, 1170, 1090 cm$^{-1}$ Step C:
4-Amino-2,5-dichloro-3-thiophenesulphonamide 7.25 g of the compound of Step B above are placed in 375 ml of a 1;1 ethanol/water mixture. The solution is heated until the product dissolves. Then 4.5 g of ammonium chloride followed by 15 g of powdered iron are added. After 10 minutes' reflux, the reaction is terminated. The insoluble material is removed by filtration and rinsed with a small amount of hot ethanol. The filtrate is evaporated off under reduced pressure. The beige precipitate that forms is collected by filtration, washed with water and then dried.

Melting point: degradation at about 120° C. IR (KBr): 3440, 3412, 3354, 3290, 1600, 1557, 1336, 1318, 1166, 1125 cm$^{-1}$ Step D: 5,7-Dichloro-4H-thieno[3,4-e][1,2,4]thiadiazine 1,1-dioxide 250 mg of the compound of Step C above are dissolved in 2.5 ml of trimethyl orthoformate. The solution is brought to boiling in an open vessel. After 1.5 hours, the reaction is complete. The solution is allowed to cool, yielding a beige precipitate which is collected by filtration, washed with diethyl ether and dried.

Melting point: 200-203° C.

EXAMPLE 1

6-Chloro-3,4-dihydro-2H-thieno[3,2-e][1,2,4]thiadiazine 1,1-dioxide 196 mg of the compound of Preparation 1 are placed in 4 ml of water. 500 mg of NaBH$_4$ are added slowly. After 15 minutes, the reaction is complete. The pH of the solution is then adjusted to 5-6 and the product is extracted using dichloromethane. The organic phase is dried over magnesium sulphate and then evaporated off under reduced pressure. The residue is taken up in a minimum of methanol, and water is added in order to cause the product to precipitate. The product is collected by filtration, washed with water and then dried.

Melting point: 154-156° C.

EXAMPLE 2

6-Chloro-4-methyl-3,4-dihydro-2H-thieno[3,2-e][1,2,4]thiadiazine 1,1-dioxide

Step A: 6-Chloro-4-methyl-4H-thieno[3,2-e][1,2,4]thiadiazine 1,1-dioxide 250 mg of the compound of Preparation 1 are placed in 5 ml of acetonitrile and 0.5 ml of dimethylformamide. 500 mg of potassium carbonate are added, as well as 0.3 ml of methyl iodide. The solution is heated at about 55° C. for about 7 hours. At the end of the reaction, the solvent is removed under reduced pressure and the residue is taken up in water. The insoluble material is quickly collected by filtration, washed with water and then dried.

Melting point: 252-254° C. IR (KBr): 3091, 2943, 1607, 1519, 1485, 1434, 1390, 1297, 1150, 1107, 1059, 1015, 835, 778, 754, 570, 541 cm$^{-1}$ Step B: 6-Chloro-4-methyl-3,4-dihydro-2H-thieno[3,2-e][1,2,4]thiadiazine 1,1-dioxide 200 mg of the compound of Step A above are dissolved in 5 ml of isopropanol. The solution is heated at about 60° C., and 400 mg of NaBH$_4$ are added. After 20 minutes, the solvent is removed under reduced pressure and the residue is taken up in water. The pH is adjusted to about 5-6 and the product is extracted with 3×10 ml of chloroform. The organic phase is then dried over magnesium sulphate, filtered and then concentrated under reduced pressure. The residue is taken up in a minimum of chloroform and then the product is precipitated by addition of hexane. The product is then collected by filtration and washed with hexane and dried.

Melting point: 174-176° C. IR: 3236, 3089, 2923, 2867, 2807, 1562, 1419, 1407, 1358, 1322, 1284, 1154, 1077, 1002, 814, 742, 680, 569, 504 cm$^{-1}$

EXAMPLE 3

6-Chloro-4-ethyl-3,4-dihydro-2H-thieno[3,2-e][1,2,4]thiadiazine 1,1-dioxide

Step A: 6-Chloro-4-ethyl-4H-thieno[3,2-e][1,2,4]thiadiazine 1,1-dioxide

This compound is obtained according to the process described in Step A of Example 2 using bromoethane instead of methyl iodide.

Melting point: 189-190° C. IR (KBr): 3098, 2982, 2943, 2878, 1609, 1518, 1480, 1464, 1437, 1400, 1300, 1255, 1173, 1161, 1121, 1015, 973, 943, 805, 766, 740, 567, 542 cm$^{-1}$ Step B: 6-Chloro-4-ethyl-3,4-dihydro-2H-thieno[3,2-e][1,2,4]thiadiazine 1,1-dioxide This compound is obtained according to the process described in Step B of Example 2 using the compound of Step A above.

Melting point: 119-120° C. IR (KBr): 3235, 2980, 2931, 2872, 1558, 1462, 1448, 1407, 1360, 1324, 1154, 1082, 1010, 798, 742, 678, 570, 501 cm$^{-1}$

EXAMPLE 4

6-Chloro-4-isopropyl-3,4-dihydro-2H-thieno[3,2-e][1,2,4]thiadiazine 1,1-dioxide

Step A: 6-Chloro-4-isopropyl-4H-thieno[3,2-e][1,2,4]thiadiazine 1,1-dioxide 400 mg of the compound of Preparation 1 are dissolved in 8 ml of acetonitrile and several drops of dimethylformamide. 800 mg of potassium carbonate are then added, followed by 0.6 ml of 2-iodopropane. The mixture is heated to about 55° C. After 8 hours, a further 0.6 ml of 2-iodopropane is added and the reaction mixture is stirred overnight. The solvent is evaporated off under reduced pressure and the residue is taken up in water. The insoluble material that is obtained is quickly collected by filtration, washed with water and dissolved in a minimum of hot methanol. Cooling yields white crystals, which are collected by filtration, washed with methanol and then dried.

Melting point: 149-150° C. IR (KBr): 3112, 2983, 1605, 1515, 1458, 1442, 1407, 1392, 1306, 1284, 1170, 1141, 1095, 1010, 805, 778, 717, 696, 670, 565, 538 cm$^{-1}$ Step B: 6-Chloro-4-isopropyl-3,4-dihydro-2H-thieno[3,2-e][1,2,4]thiadiazine 1,1-dioxide This compound is obtained according to the process described in Step B of Example 2 using the compound of Step A above.

Melting point: 100-102° C. IR (KBr): 3267, 3241, 2970, 2954, 1545, 1460, 1445, 1409, 1332, 1301, 1156, 1123, 1025, 786, 742, 692, 678, 566, 502 cm$^{-1}$

EXAMPLE 5

5,7-Dichloro-3,4-dihydro-2H-thieno[3,4-e][1,2,4]thiadiazine 1,1-dioxide 800 mg of the compound of Preparation 2 are suspended in 15 ml of water, and 2 g of finely ground NaBH$_4$ are slowly added thereto. After 10 minutes' stirring at ambient temperature, the reaction mixture is adjusted to pH 6 using 6N hydrochloric acid and extracted twice with dichloromethane. The organic phase is dried over magnesium sulphate and the solvent is removed under reduced pressure. The residue is dissolved in a minimum of methanol and treated with activated carbon, and then water is added until precipitation is complete. The precipitate is then collected by filtration and purified twice by dissolution in a minimum of methanol and addition of water.

Melting point: 125-130° C.

EXAMPLE 6

5,7-Dichloro-4-methyl-3,4-dihydro-2H-thieno[3,4-e][1,2,4]thiadiazine 1,1-dioxide Step A: 5,7-Dichloro-4-methyl-4H-thieno[3,4-e][1,2,4]thiadiazine 1,1-dioxide 200 mg of the compound of Preparation 2 are dissolved in 2 ml of nitroethane and 2 ml of dimethylformamide. The solution is heated to 60° C. Then 0.2 g of potassium carbonate is added, followed by 0.2 ml of iodomethane. The solution is stirred for 2 hours. The solvents are then removed under reduced pressure. The residue is taken up in water. The insoluble material is quickly collected by filtration, washed with water and dried.

Melting point: 202-207° C. IR (KBr): 3436, 3043, 2960, 1607, 1551, 1472, 1439, 1400, 1356, 1347, 1308, 1202, 1145, 1101, 1060, 862, 789, 744, 664, 573, 527 cm$^{-1}$ Step B: 5,7-Dichloro-4-methyl-3,4-dihydro-2H-thieno[3,4-e][1,2,4]thiadiazine 1,1-dioxide 500 mg of the compound of Step A above are dissolved in 15 ml of isopropanol at 60° C. 1.5 g of finely ground NaBH$_4$ are then added to the solution. After 30 minutes, the isopropanol is evaporated off under reduced pressure. The residue is then taken up in water and the pH of the solution is adjusted to 7. The solution is then extracted with chloroform (3×40

EXAMPLE 7

5,7-Dichloro-4-ethyl-3,4-dihydro-2H-thieno[3,4-e][1,2,4]thiadiazine 1,1-dioxide Step A: 5,7-Dichloro-4-ethyl-4H-thieno[3,4-e][1,2,4]thiadiazine 1,1-dioxide 4 g of the compound of Step C of Preparation 2 are placed in 20 ml of triethyl orthoformate and heated at 170° C. for 30 minutes in an open vessel. The suspension is then cooled on ice. The precipitate that forms is collected by filtration, washed with n-hexane and dried.

Melting point: 172-175° C.

Step B: 5,7-Dichloro-4-ethyl-3,4-dihydro-2H-thieno[3,4-e][1,2,4]thiadiazine 1,1-dioxide 0.5 g of the compound of Step A above is dissolved in 20 ml of isopropanol. The solution is heated to 60° C., and 1.5 g of finely ground NaBH$_4$ are added thereto. After 30 minutes, the solvent is removed under reduced pressure. The residue is then taken up in 30 ml of water and the suspension is neutralised by addition of 6N hydrochloric acid. The solution is extracted twice with chloroform. The organic phase is dried over magnesium sulphate and the solvent is removed under reduced pressure. The residue is taken up in hexane, collected by filtration, washed with n-hexane and dried.

Melting point: 144-147° C.

EXAMPLE 8

6-Chloro-N,4-diethyl-3,4-dihydro-2H-thieno[3,2-e][1,2,4]thiadiazine-2-carboxamide 1,1-dioxide 200 mg of the compound of Example 3 are dissolved in 1.5 ml of CH$_3$CN. 1 ml of ethyl to isocyanate and 0.2 ml of triethylamine are then added to the solution. The reaction mixture is stirred at ambient temperature for 2 hours At the end of that period, the solvents are removed in vacuo. The residue is dissolved in a minimum of acetone. The product is then precipitated by gradual addition of water. The product is quickly collected by filtration, washed with water and then dried.

Melting point: 80-81° C.

EXAMPLE 9

6-Chloro-N-ethyl-4-isopropyl-3,4-dihydro-2H-thieno[3,2-e][1,2,4]-thiadiazine-2-carboxamide 1,1-dioxide This compound is obtained according to the process of Example 8 using the compound of Example 4 instead of the compound of Example 3.

Melting point: 72-74° C.

EXAMPLE 10

5,7-Dichloro-N-ethyl-4-methyl-3,4-dihydro-2H-thieno[3,4-e][1,2,4]-thiadiazine-2-carboxamide 1,1-dioxide This compound is obtained according to the process of Example 8 using the compound of Example 6 instead of the compound of Example 3.

Melting point: 87-88° C.

EXAMPLE 11

6-Chloro-4-(2-fluoroethyl)-3,4-dihydro-2H-thieno[3,2-e][1,2,4]-thiadiazine 1,1-dioxide Step A: 6-Chloro-4-(2-fluoroethyl)-4H-thieno[3,2-e][1,2,4]thiadiazine 1,1-dioxide 500 mg of the compound of Preparation 1 are suspended in 10 ml of acetonitrile. 10 drops of DMF, 1 g of potassium carbonate and 0.3 ml of 1-fluoro-2-iodoethane are added to the suspension. The reaction mixture is heated at 70° C. for 35 hours, with stirring. After cooling the reaction mixture, the insoluble material is removed by filtration. The solvents are removed by evaporation under reduced pressure. The solid residue that is obtained is taken up in 10 ml of water and is immediately collected by filtration. The product so obtained is recrystallised from ethyl acetate.

Melting point: 185-187° C.

Step B: 6-Chloro-4-(2-fluoroethyl)-3,4-dihydro-2H-thieno[3,2-e][1,2,4]-thiadiazine 1,1-dioxide 100 mg of the compound obtained in Step A above are dissolved in 4 ml of isopropanol. The mixture is heated to 60° C., then 200 mg of sodium borohydride are added. After minutes at that temperature, the solvent is evaporated off under reduced pressure. The residue that is obtained is taken up in 10 ml of water, cooled in an ice bath and adjusted to pH 4 by addition of 6N hydrochloric acid. The insoluble material is collected by filtration and washed with water. The product is then dissolved in a minimum of chloroform and precipitated by addition of n-hexane. The precipitate is then collected by filtration.

Melting point: 141-144° C.

EXAMPLE 12

4,7-Dimethyl-3,4-dihydro-2H-thieno[2,3-e][1,2,4]thiadiazine 1,1-dioxide

Step A: 7-Methyl-4H-thieno[2,3-e][1,2,4]thiadiazine 1,1-dioxide 200 mg of 2-amino-4-methylthiophene-3-sulphonamide, the preparation of which is described in patent WO 99/03861, are dissolved in 1.5 ml of trimethyl orthoformate. The mixture is heated at 90° C. for 2 hours in an open vessel. After evaporation of the solvent under reduced pressure, the residue is taken up in 3 ml of ethyl acetate. The resulting insoluble material is collected by filtration, washed with diethyl ether and dried.

Melting point: 195-198° C.

Step B: 4,7-Dimethyl-4H-thieno[2,3-e][1,2,4]thiadiazine 1,1-dioxide 150 mg of the compound obtained in Step A above are suspended in 5 ml of acetonitrile. 300 mg of potassium carbonate and 0.15 ml of iodomethane are added thereto. The reaction mixture is heated at 65° C. for 30 minutes, with stirring. After evaporation of the solvents under reduced pressure, the residue is taken up in 5 ml of water and then collected by filtration, washed with water and dried.

Melting point: 265-270° C.

Step C: 4,7-Dimethyl-3,4-dihydro-2H-thieno[2,3-e][1,2,4]thiadiazine 1,1-dioxide 240 mg of sodium borohydride are added to 120 mg of the compound obtained in Step B above dissolved in 6 ml of isopropanol. The mixture is heated at 50° C. for 10 minutes. The solvent is removed under reduced pressure, then the residue that is obtained is taken up in 5 ml of water. The pH of the solution is adjusted to 4 by addition of 6N hydrochloric acid. The precipitate is collected by filtration, washed with water and dried.

Melting point: 171-173° C.

EXAMPLE 13

6-Chloro-4-isopropylmethyl-3,4-dihydro-2H-thieno[3,2-e][1,2,4]-thiadiazine 1,1-dioxide Step A: 6-Chloro-4-fluoromethyl-4H-thieno[3,2-e][1,2,4]thiadiazine 1,1-dioxide 500 mg of the compound of Preparation 1 are suspended in 15 ml of acetonitrile. 500 mg of potassium carbonate and 1 ml of bromofluoromethane are added thereto. The mixture is placed in a sealed autoclave and heated at 70° C. for 8 hours. The insoluble material is then removed by filtration. After evaporation of the solvent, the residue is taken up in 20 ml of water and collected on a filter. The solid so obtained is recrystaillised from methanol.

Step B: 6-Chloro-4-isopropylmethyl-3,4-dihydro-2H-thieno[3,2-e][1,2,4]-thiadiazine 1,1-dioxide 400 mg of sodium borohydride are added to 200 mg of the compound obtained in Step A above suspended in 8 ml of isopropanol. The mixture is heated at 50° C. for 10 minutes, with stirring. The insoluble material is removed by filtration. After evaporation of the solvent under reduced pressure, the residue is taken up in 1 ml of an ethyl acetate/n-hexane mixture (15/5) and purified by column chromatography in the same mobile phase. After evaporation of the solvents, the residue is dissolved in 1 ml of methanol and precipitated in water. The solid product so obtained is collected by filtration, washed with water and dried.

Melting point: 65-68° C.

Pharmacological Study of Compounds of the Invention

EXAMPLE A

Study of the Excitatory Currents Induced by AMPA in Xenopus Oocytes mRNA's are prepared from cerebral cortex of male Wistar rats by the guanidinium thiocyanate/phenol/chloroform method. The poly (A⁺) mRNA's are isolated by chromatography on oligo-dT cellulose and injected at a level of 50 ng per oocyte. The oocytes are incubated for 2 to 3 days at 18° C. to permit expression of the receptors and are then stored at 8-10° C.

Electrophysiological recording is carried out in a Plexiglass® chamber at 20-24° C. in OR2 medium (J. Exp. Zool., 1973, 184, 321-334) by the "voltage-clamp" method using two electrodes, a third electrode being placed in the bath serving as reference.

All the compounds are applied via the incubation medium and the electric current is measured at the end of the application period. (S)-AMPA is used in a concentration of 10 μM. For each compound studied, the concentration that doubles (EC2X) or quintuples (EC5X) the intensity of the current induced by AMPA alone (5 to 50 nA) is determined.

The compounds of the invention potentiate the excitatory effects induced by (S)-AMPA to a very considerable degree. By way of examples, the compounds of Examples 4 to 6 exhibit the EC2X and EC5X values mentioned in the table below:

| Compound | EC2X (μM) | EC5X (μM) |
|---|---|---|
| Example 4 | 4.2 ± 0.7 | 11 ± 3 |
| Example 6 | 5.4 ± 2.8 | 11.3 ± 4.9 |

EXAMPLE B

Study of the Excitatory Postsynaptic Potentials (EPSP) Induced by Electric Stimulation on Rat Hippocampus Sections Transverse hippocampus sections (500 μM) of male Wistar rats are prepared with the aid of a tissue chopper and then incubated for 45 minutes in a calcium-free medium comprising $Mg^{2+}$ (10 mM). They are then stabilised in Krebs adjusted to pH 7.35 and oxygenated with $O_2/CO_2$ (95%/5%) at ambient temperature.

The sections are submersed at 30° C. and the excitatory postsynaptic potentials (EPSP) are recorded in the dendritic field of the granule cells of the dentate gyrus during stimulation (50-100 μA, 50 μsec) every 30 seconds of the perforant path by means of a bipolar tungsten electrode.

The EPSP are acquired and analysed by means of an A-D converter, a TL-1 interface and "pCLAMP" software.

The amplitude and duration of the EPSP are evaluated on the negative wave relative to the base current.

The compounds are applied for a period of 10 minutes in the superfusion bath comprising $MgSO_4$ (1 mM) in order to block activation of the NMDA receptors. For each compound, the concentration that increases by 50% the amplitude (A50) or the duration (D50) of the PSEP is determined.

The compounds of the invention increase considerably the amplitude and duration of the excitatory postsynaptic field potentials recorded on rat hippocampus sections.

| PHARMACEUTICAL COMPOSITION: Preparation formulation for 1000 tablets each comprising 100 mg | |
|---|---|
| compound of Example 3 | 100 g |
| hydroxypropylcellulose | 2 g |
| wheat starch | 10 g |
| lactose | 100 g |
| magnesium stearate | 3 g |
| talc | 3 g |

The invention claimed is:
1. A compound selected from those of formula (I):

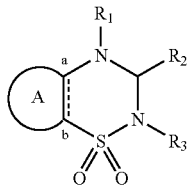

wherein:
A represents a thienyl, furyl or pyrrolyl group selected from the groups $A_1$, $A_2$, and $A_3$:

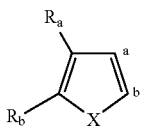 $A_1$

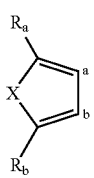 $A_2$

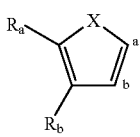 $A_3$ wherein X represents sulphur, oxygen or nitrogen and $R_a$ and $R_b$, which may be identical or different, each independently of the other represents hydrogen, linear or branched ($C_1$-$C_6$)alkyl (optionally substituted by one or more fluorine), linear or branched ($C_1$-$C_6$)alkoxy, halogen, hydroxy, amino (optionally substituted by linear or branched ($C_1$-$C_6$)alkylcarbonyl or by one or two linear or branched ($C_1$-$C_6$)alkyl), carboxyl or linear or branched ($C_1$-$C_6$)alkoxycarbonyl, an oxathiol group selected from the groups $A_4$, $A_5$, $A_6$, and $A_7$:

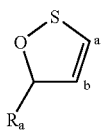 $A_4$

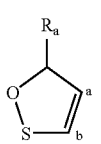 $A_5$

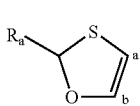 $A_6$

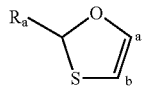 $A_7$ wherein $R_a$ is as defined hereinbefore,
a thiazole group selected from the groups $A_8$ and $A_9$:

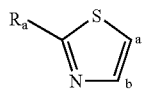 $A_8$

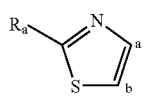 $A_9$ wherein $R_a$ is as defined hereinbefore,
an isothiazole group selected from the groups $A_{10}$ and $A_{11}$:

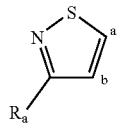 $A_{10}$

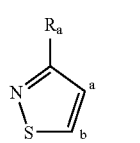 $A_{11}$ wherein $R_a$ is as defined hereinbefore,
an oxazole group selected from the groups $A_{12}$, $A_{13}$, $A_{14}$, and $A_{15}$:

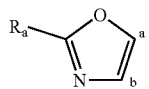 $A_{12}$

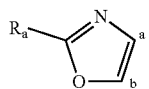 $A_{13}$

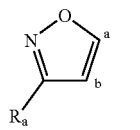 $A_{14}$

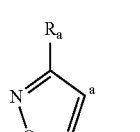 $A_{15}$ wherein $R_a$ is as defined hereinbefore, or an imidazole group of formula $A_{16}$:

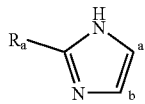

wherein $R_a$ is as defined hereinbefore,

----- represents a single bond or a double bond, $R_1$ represents hydrogen, linear or branched ($C_1$-$C_6$)alkyl optionally substituted by one or more fluorine atoms, one or more halogen atoms other than fluorine, or ($C_1$-$C_6$)alkoxy-($C_1$-$C_6$)alkyl in which each alkyl moiety may be linear or branched, $R_2$ represents hydrogen or linear or branched ($C_1$-$C_6$)alkyl optionally substituted by one or more fluorine atoms, or a plurality of halogen atoms other than fluorine, $R_3$ represents hydrogen or a group selected from linear or branched ($C_1$-$C_6$)alkyl, CONHR' and SO$_2$NHR' wherein R' represents linear or branched ($C_1$-$C_6$)alkyl, its enantiomers and diastereoisomers, and addition salts thereof with a pharmaceutically acceptable acid or base.

2. A compound of claim 1, wherein A represents a thienyl group selected from the groups $A_1$, $A_2$ and $A_3$ wherein X represents sulphur, its enantiomers and diastereoisomers, and also addition salts thereof with a pharmaceutically acceptable acid or base.

3. A compound of claim 1, wherein A represents a thienyl group selected from the groups $A_1$ and $A_2$ wherein X represents sulphur, its enantiomers and diastereoisomers, and addition salts thereof with a pharmaceutically acceptable acid or base.

4. A compound of claim 2, wherein $R_a$ and $R_b$ each independently of the other represents hydrogen or chlorine, its enantiomers and diastereoisomers, and addition salts thereof with a pharmaceutically acceptable acid or base.

5. A compound of claim 1, wherein $R_1$ represents hydrogen or linear or branched ($C_1$-$C_6$)alkyl, its enantiomers and diastereoisomers, and addition salts thereof with a pharmaceutically acceptable acid or base.

6. A compound of claim 5, wherein $R_1$ represents methyl, ethyl or isopropyl, its enantiomers and diastereoisomers, and addition salts thereof with a pharmaceutically acceptable acid or base.

7. A compound of claim 1, wherein $R_2$ represents hydrogen, its enantiomers and diastereoisomers, and addition salts thereof with a pharmaceutically acceptable acid or base.

8. A compound of claim 1, wherein $R_3$ represents hydrogen or CONHR', its enantiomers and diastereoisomers, and addition salts thereof with a pharmaceutically acceptable acid or base.

9. A compound of claim 1 which is selected from:
  6-chloro-4-ethyl-3,4-dihydro-2H-thieno[3,2-e][1,2,4]thiadiazine 1,1-dioxide,
  6-chloro-4-isopropyl-3,4-dihydro-2H-thieno[3,2-e][1,2,4]thiadiazine 1,1-dioxide, and
  5,7-dichloro-4-methyl-3,4-dihydro-2H-thieno[3,4-e][1,2,4]thiadiazine 1,1-dioxide.

10. A pharmaceutical composition comprising as active ingredient a compound of claim 1, in combination with one or more inert, non-toxic, pharmaceutically acceptable carriers.

11. A method of treating a living animal body, including a human, afflicted with a condition selected from anxiety and depression, comprising the step of administering to the living animal body, including a human, an amount of a compound of claim 1 which is effective for alleviation of the condition.

* * * * *